United States Patent [19]

Lewis et al.

[11] Patent Number: 5,250,027
[45] Date of Patent: Oct. 5, 1993

[54] PERISTALTIC INFUSION DEVICE WITH BACKPACK SENSOR

[75] Inventors: Thomas G. Lewis, Fairview Heights, Ill.; Denis Y. Yerlikaya, Des Peres; Eugene F. Schrader, St. Louis, both of Mo.

[73] Assignee: Sherwood Medical Company, St. Louis, Mo.

[21] Appl. No.: 774,014

[22] Filed: Oct. 8, 1991

[51] Int. Cl.$^5$ .............................................. A61M 1/00
[52] U.S. Cl. ........................................ 604/65; 604/67; 128/DIG. 12
[58] Field of Search .................... 604/65, 67, 151-153; 128/DIG. 12, DIG. 13

[56] References Cited

U.S. PATENT DOCUMENTS

| | | | |
|---|---|---|---|
| 3,228,474 | 1/1966 | Huthsing, Jr. | 169/31 |
| 3,731,679 | 5/1973 | Wilhelmson et al. | 128/DIG. 12 |
| 3,972,648 | 8/1976 | Jutte | 417/53 |
| 4,080,967 | 3/1978 | O'Leary | 604/152 |
| 4,311,050 | 1/1982 | Bessman | 73/427 |
| 4,397,639 | 8/1983 | Eschweilwer et al. | 604/153 |
| 4,416,595 | 11/1983 | Cromie | 417/476 |
| 4,453,931 | 6/1984 | Pastrone | 604/153 |
| 4,479,761 | 10/1984 | Bilstad et al. | 417/395 |
| 4,496,351 | 1/1985 | Hillel et al. | 604/250 |
| 4,507,112 | 3/1985 | Hillet et al. | 604/65 |
| 4,513,796 | 4/1985 | Miller et al. | 141/83 |
| 4,519,792 | 5/1985 | Dawe | 604/152 |
| 4,545,783 | 10/1985 | Vaughn | 604/259 |
| 4,557,725 | 12/1985 | Heyne et al. | 128/DIG. 12 |
| 4,657,486 | 4/1987 | Stempfle et al. | 417/12 |
| 4,684,367 | 8/1987 | Schaffer et al. | 604/140 |
| 4,688,595 | 8/1987 | Srebnick et al. | 137/343 |
| 4,690,673 | 9/1987 | Bloomquist | 604/67 |
| 4,699,613 | 10/1987 | Donawick et al. | 604/80 |
| 4,720,636 | 1/1988 | Benner, Jr. | 250/573 |
| 4,722,734 | 2/1988 | Kolln | 604/151 |
| 4,758,228 | 7/1988 | Williams | 604/153 |
| 4,808,167 | 2/1989 | Mann et al. | 128/DIG. 12 |
| 4,828,545 | 5/1989 | Epstein et al. | 604/67 |
| 4,832,584 | 5/1989 | Nassif | 417/477 |
| 4,836,752 | 6/1989 | Burkett | 604/67 |
| 4,884,013 | 11/1989 | Jackson et al. | 318/481 |
| 4,890,984 | 1/1990 | Alderson et al. | 417/234 |
| 4,913,703 | 4/1990 | Pasqualucci et al. | 604/153 |
| 4,946,439 | 8/1990 | Eggers | 604/67 |
| 5,057,081 | 10/1991 | Sunderland | 604/153 |
| 5,078,683 | 1/1992 | Sancoff et al. | 128/DIG. 13 |
| 5,097,255 | 3/1992 | Chen | 128/DIG. 13 |
| 5,112,019 | 5/1992 | Metzler et al. | 604/65 |
| 5,116,203 | 5/1992 | Natwick et al. | 604/153 |

FOREIGN PATENT DOCUMENTS

| | | | |
|---|---|---|---|
| 3606930 | 9/1987 | Fed. Rep. of Germany | . |
| 2162241 | 7/1973 | France | . |
| 2444293 | 8/1980 | France | 128/DIG. 12 |
| 8500523 | 2/1985 | PCT Int'l Appl. | 604/151 |
| 9007947 | 7/1990 | PCT Int'l Appl. | . |

OTHER PUBLICATIONS

Ross Laboratories, introducing flexiflo Companion Enteral Nutrition Pump, Feb. 1988, 2 pages.
Ross Laboratories, Flexiflo Companion Enteral Nutrition Pump Operating Manual, Aug. 1987, pp. 1-16.
Fresenius AG, Frenta-System for Continuous Tube Feeding, Instruction for Use, date unknown, 13 pages.

*Primary Examiner*—Ralph Lewis
*Attorney, Agent, or Firm*—Richard D. Allison; Gene B. Kartchner; Montgomery W. Smith

[57] ABSTRACT

The present invention relates to a sensed member and sensing member for use on a medical fluid infusion device and support device wherein the fluid infusion device is usable in a conventional manner such as on an IV pole and in an ambulatory manner such as in a support device for use in an ambulatory backpack. The sensing member of the present invention detects when the fluid infusion device is to be used in an ambulatory manner to adjust the operation of the infusion control member to account for the difference in fluid flow rates caused by the different fluid pressures within the fluid delivery set when the fluid infusion device is used in a conventional manner and an ambulatory manner.

8 Claims, 6 Drawing Sheets

PERISTALTIC INFUSION DEVICE WITH BACKPACK SENSOR

FIELD OF THE INVENTION

The present invention relates to a sensing mechanism which allows a fluid infusion device to be used as an ambulatory device, such as in a backpack, or in a conventional manner such as on an IV pole. The present invention is more particularly related to a sensing mechanism which adjusts the operation of a flow control member according to whether the infusion device is used as an ambulatory device or in a non-ambulatory manner.

BACKGROUND OF THE INVENTION

The assignee of the present invention presently markets an enteral fluid infusion device under the trademark "KANGAROO." This system includes a fluid infusion device and a disposable fluid delivery set, which includes a fluid inlet tube, a drip chamber which is arranged to be mounted in a recess on the fluid infusion device, a mounting member, also arranged to be mounted in a recess on the fluid infusion device, an outlet tube connected to the mounting member and a stretchable pump tube or silicone tube which connects the drip chamber to the mounting member and engages a motor driven infusion control member or rotor on the fluid infusion device to form a peristaltic infusion pump.

As disclosed in U.S. Pat. No. 4,913,703 granted to Pasqualucci et al. and assigned to the assignee of the present invention, the mounting member preferably includes a magnetic member which is sensed by a sensor such as a magnetic sensor on the infusion device to enable operation of the fluid infusion device only when the pump tube is operatively mounted or aligned about the rotor of the fluid infusion device. The disclosure of U.S. Pat. No. 4,913,703 is incorporated herein by reference as if fully set forth herein below.

The preferred form of the motor units used in the "KANGAROO" fluid infusion devices is disclosed in U.S. Pat. No. 4,884,013 granted to Jackson et al. and assigned to the assignee of the present invention. The disclosure of this patent is incorporated herein as if fully set forth below. As disclosed in the Jackson et al. patent, a means for detecting the completion of an operating cycle of the pump operating means and also operating the motor unit until the completion of the operating cycle is detected. Operation of the motor unit is repeated at variable time intervals or cycle times which are selected in accordance with the desired rate of fluid delivery. More specifically, the motor unit operates under the control of a microcomputer which is provided with a first control program. A programmable interval timer is provided for operating and initiating the microcomputer. Additionally, a clock operating at approximately 4 Mhz, provides clock pulses to the present system. The various controls of the motor unit are proved as input signals to the microcomputer. Additional inputs to the microcomputer are provided by magnetic sensors which sense the mounting member (as set forth more fully in U.S. Pat. No. 4,913,703 discussed above) and which sense a plurality of magnets on the rotor as the magnets rotate past another magnetic field sensor during each operating cycle.

One common feature of many of the commercially available infusion devices is that the flow of fl id through the fluid delivery set is not directly measured. Instead, the flow of fluid through the fluid delivery set is estimated based on a predetermined or average volume of fluid located between a pair of members which compress or pinch the tubing and push the fluid through the fluid delivery set. These members may be oriented linearly such as in a linear peristaltic infusion device or as part of a rotor in a rotary peristaltic infusion device. Because the flow of fluid through the fluid delivery set is estimated, there are a number of factors which may affect the actual flow of fluid to the patient. Two of the most correctable causes of inaccurate fluid delivery to a patient relate to variances in the inner diameter of the pump tube and variances in the length of the pump tube used on the fluid delivery set. The incidence of inaccurate fluid delivery with either of these causes may be significantly reduced by carefully monitoring the critical dimensions of the fluid delivery sets.

The development of a fluid infusion device which is designed for ambulatory use and in a conventional setting such as a hospital, requires that another cause of inaccurate fluid delivery be addressed. This further cause of inaccurate fluid delivery relates to the height of the fluid reservoir above the infusion control member on the fluid infusion device (referred to herein as the head height). When a fluid infusion device is used on an IV pole, the fluid reservoir is typically hung two or more feet above the infusion control member. The gravitational flow of fluid from the fluid reservoir to the infusion control member causes a first fluid pressure within the fluid delivery set. This fluid pressure has a particularly pronounced affect on the stretchable pump tube portion of the fluid delivery set. In most currently available fluid infusion devices, the fluid delivery set is particularly designed for use in this situation and the operation of the infusion control device is programmed based on this amount fluid pressure inside the fluid delivery set.

During ambulatory use, the fluid reservoir is typically positioned adjacent to the fluid infusion device such that the outlet of the fluid reservoir is positioned at or near the height of the infusion control member. This causes a second fluid pressure in the fluid delivery set which is significantly lower than the first fluid pressure created when the fluid infusion device is used on an IV pole. Because of the lower second fluid pressure when the fluid infusion device is used as an ambulatory device, less fluid will be trapped between the members in the infusion control member. This occurs because the second fluid pressure will cause less stretching of the pump tube than the first fluid pressure. Therefore, significantly less fluid may be delivered to the patient during the same number of revolutions of the rotor on a rotary peristaltic infusion device or the same number of movements of the members on a linear peristaltic infusion device. Conversely, if the fluid reservoir is somehow hung a greater than normal distance above the infusion control member, a higher fluid pressure will be present in the fluid delivery set and excess fluid will be delivered to the patient.

Currently, a need remains for a device which will compensate for the changes in fluid pressure within the fluid delivery set due to the relative position of the fluid reservoir with respect to the infusion control member on the fluid infusion device.

SUMMARY OF THE INVENTION

It is an object of the present invention to provide a sensing mechanism which will adjust the operation of the infusion control member on a fluid infusion device according to the intended use of the fluid infusion device.

It is a further object of the present invention to provide a means for correcting inaccurate actual flow rates caused by changes in the head height between the fluid reservoir and the infusion control member of the fluid infusion device.

The present invention is intended to be applicable to all medical fluid delivery systems which include a fluid delivery set arranged to be mounted on a corresponding fluid infusion control member. In particular, the present invention is intended to be used in medical fluid delivery systems where the height of the fluid reservoir above the infusion control member on the fluid infusion device may be varied according to the intended use of the fluid delivery system. Therefore, in a broad sense, the present invention is directed to a fluid infusion system consisting of a fluid reservoir and a fluid infusion device wherein the fluid infusion device includes an infusion control member and a sensing means or a sensed means thereon and the fluid reservoir includes the other of the sensing means or sensed means operatively associated therewith such that the operation of the fluid control member is adjusted according to the input of the sensing means to accurately infuse fluid into the patient based on the head height between the fluid reservoir and the infusion control member or the fluid pressure within the fluid delivery set.

In the simplest and preferred form of the present invention, the fluid infusion device includes a sensor thereon to detect when the fluid infusion device is in the support structure of an ambulatory backpack device. As described more fully below, the support structure includes a magnetic member therein which is detected by a magnetic field sensitive sensor on the fluid infusion deice. When the sensor detects the magnet, the input from the sensor to the microprocessor causes the microprocessor to select a modified control program which then adjusts the operation of the motor unit by a known amount to compensate for the reduced head height or lower fluid pressure within the fluid delivery set. As an alternate to the use of a modified control program, the primary control program may be substituted with a secondary control program when the sensor detects the magnet to adjust the operation of the motor control unit.

An advantage of the present invention is that it allows a fluid infusion device to be truly usable in an ambulatory situation and in a conventional situation while increasing the accuracy of the actual rate and amount of fluid delivered to the patient.

Another advantage of the present invention is that it may be used to increase the accuracy of nearly any fluid infusion device which is designed for use in a number of different settings.

A further advantage of the present invention is that it allows standard fluid delivery sets to be used with a fluid infusion device in both ambulatory and conventional settings.

Yet another advantage of the present invention is that it provides a simple and inexpensive way to adjust the operation of the infusion control member of the fluid infusion device based on the intended use of the fluid infusion device.

DETAILED DESCRIPTION OF THE PREFERRED EMBODIMENTS

As shown in the drawings, a preferred embodiment of a medical fluid infusion device made in accordance with the principles of the present invention, referred to herein generally by the reference numeral 10, is provided for use in an ambulatory manner on a support device 12 or in a conventional manner on an IV pole 14.

The preferred form of the fluid infusion device 10 as shown and described herein is more fully disclosed in a copending U.S. patent application assigned U.S. Ser. No. 07/538,791 filed on Jun. 15, 1990. The preferred form of the support device 12 shown and described herein is more fully disclosed in a copending U.S. patent application assigned U.S. Ser. No. 07/679,886 filed on Apr. 3, 1991. Both of these copending patent applications are commonly assigned to Sherwood Medical Company and are incorporated herein by reference as if fully set forth below.

Figure 1:
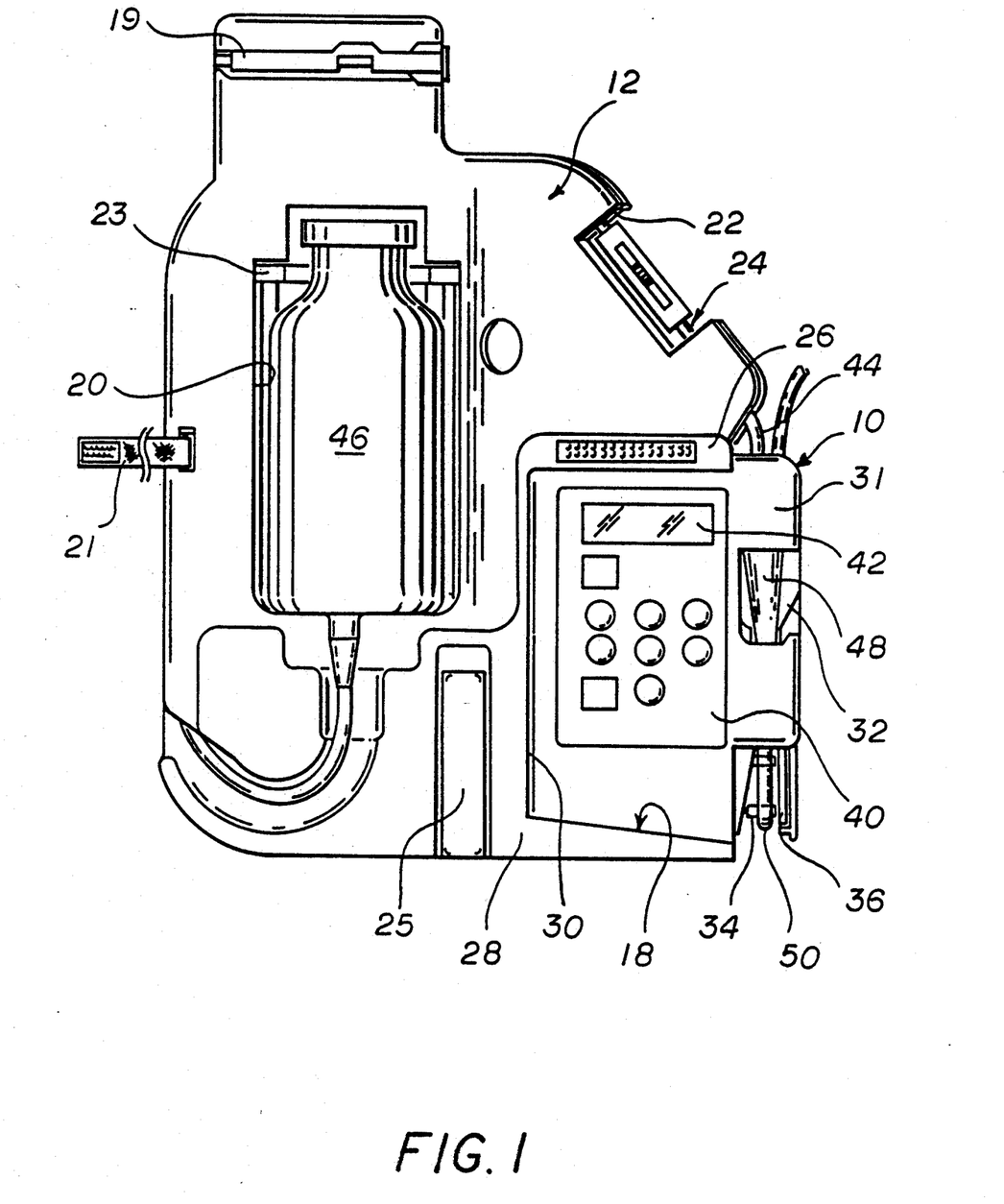
FIG. 1 is a front perspective view of a medical fluid delivery system incorporating the present invention.

As shown in FIG. 1, the support device 12 includes a generally rectangular rigid body formed of rigid polymeric material or other lightweight material such as wood, metal alloy, etc. The support device 12 is particularly designed for use in a flexible backpack which includes flexible shoulder straps as described more fully in the above referenced copending patent application. The body is adapted to receive and retain a fluid delivery set 16 and a fluid infusion device 10 of a fluid delivery system thereon. Specifically, the body forms an infusion device receiving compartment 18 adapted to receive a standard fluid infusion device 10 therein, a fluid reservoir receiving compartment 20 adapted to at least partially receive a container from a standard fluid delivery set 16 thereon, a tube channel 22 adapted to receive the tube of a standard fluid delivery set 16, and a valve receiving recess 24 adapted to receive a pinch valve located on the tubing of the fluid delivery set 16.

The support device 12 also includes a plurality of fastening elements which are adapted for use in securing the fluid delivery system to the body during use. These elements include an adjustable lid clamp 19; a securing strap 21; a saddle bracket 23 and a pump locking mechanism formed as a part of the support device 12 and described more fully in the above-identified copending patent application. Finally, if desired, an extendable leg 25 may be located in an elevated section of the base of the support device 12 so as to be flush therewith when the leg is in its retracted position, and to be extendable to a position perpendicular therewith and parallel to base in its extended position. The leg may also have an identical counterpart on the back surface of the body of the support device 12.

Figure 2:
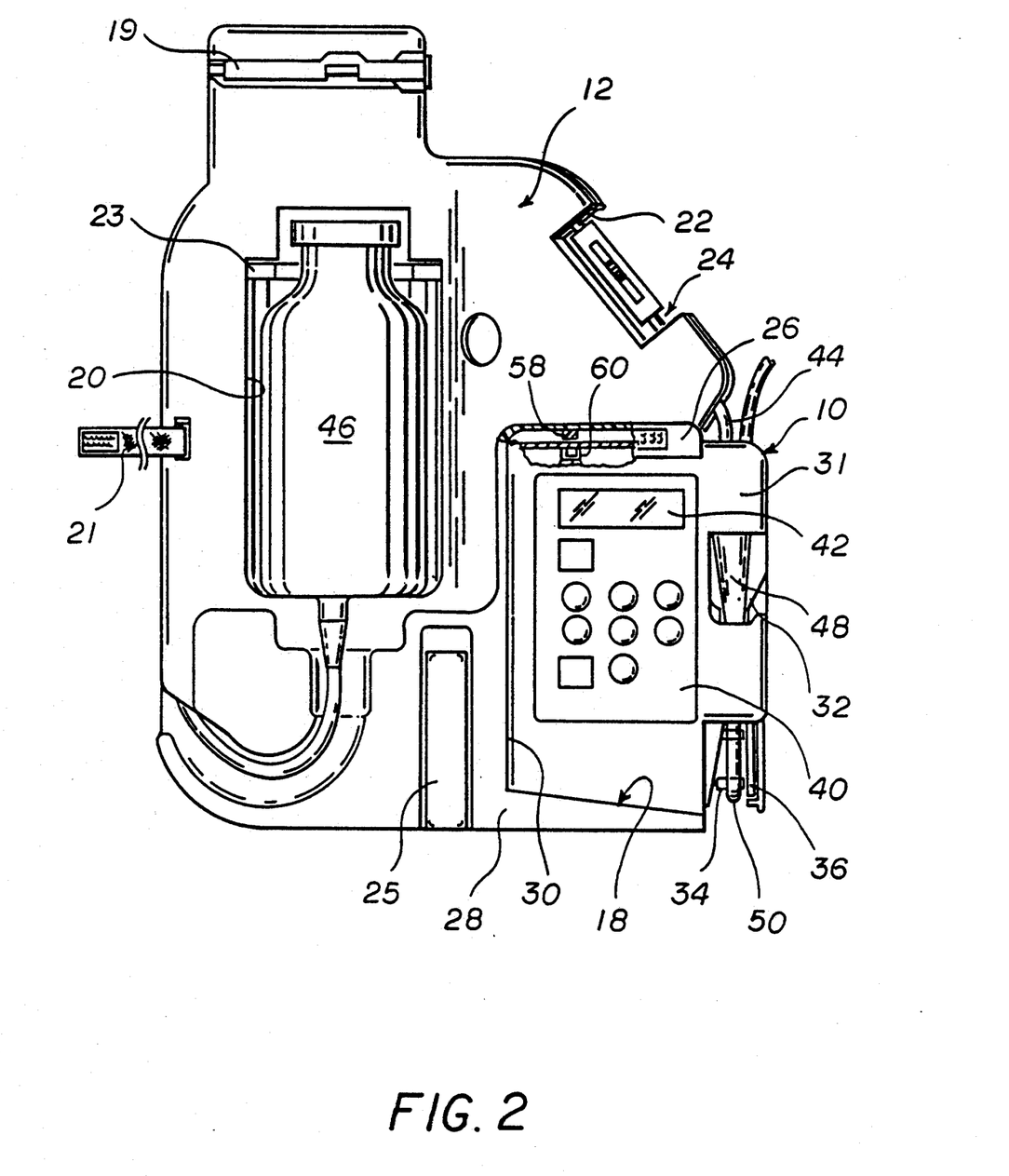
FIG. 2 is a front perspective view, partially in cross-section showing a sensor and sensed means in accordance with the present invention.

As best shown in FIGS. 1 and 2, the device receiving compartment 18 is formed of a generally C-shaped cavity having an upper and lower U-shaped channel 26 and 28, respectively, which are sized to receive the fluid infusion device 10 in a sliding relationship. The U-shaped channels 26 and 28 are designed to allow the fluid infusion device 10 to slide therein until the fluid infusion device 10 abuts with the abutment surface 30.

The preferred form of the present invention includes a fluid infusion device 10 particularly adapted for the controlled delivery of enteral fluid to a patient. It should be understood that although the present invention is described herein with reference to a rotary type of peristaltic fluid infusion device, the present invention is readily adaptable for use with nearly any type of rotary or linear infusion device wherein it is desired to deliver a medical fluid at a controlled rate through a tubular member that is mounted along at least a portion of the fluid infusion device 10.

The fluid infusion device 10 of the present invention consists generally of a rectangularly-shaped housing assembly 31 having a swing arm 32 pivotally mounted on the lower side surface thereof with a partially enclosed rotor 36 extending therefrom. The rotor 36 preferably includes a plurality of rollers 34 thereon. As shown in FIG. 2, the front surface 38 of the housing assembly 31 is a generally flat and rectangularly-shaped surface which includes a control panel section 40 and an alpha numeric LED display section 42.

As described briefly above, the fluid infusion device 10 of the preferred embodiment is particularly designed for use with a conventional fluid delivery set 40 as disclosed in U.S. Pat. No. 4,913,703. The fluid delivery set 16 allows medical fluid to flow therethrough and generally consists of an elongate and flexible inlet tube 44 which is connected to fluid reservoir 46 at one end and the top of a drip chamber assembly 48 at the other end. The pump tube 50 preferably consists of a predetermined length of resilient and compressible silicone tubing having a first predetermined internal diameter in the relaxed condition and a second predetermined internal diameter in the stretched condition as described hereinafter. The second end of the pump tube 50 is connected to a circular mounting or connector member 52. The mounting member 52 preferably includes a cylindrically-shaped magnet 54 thereon, the function of which is described more fully in U.S. Pat. No. 4,913,703. An elongate outlet tube 56 includes a first end which is connected to the mounting member 54 and a second end (not shown) which is adapted to deliver the medical fluid to the patient.

Figure 5:
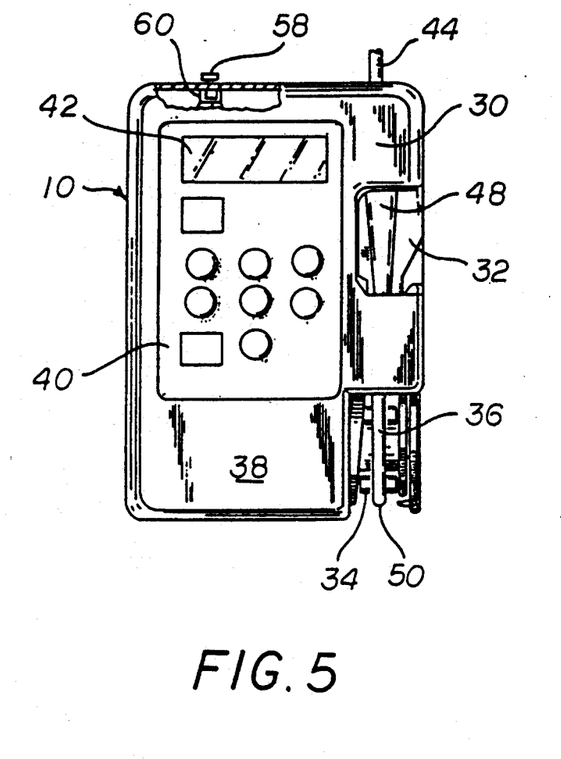
FIG. 5 is a front diagrammatic perspective view, partially in cross section, of the preferred form of the fluid infusion device showing the relative positioning of the sensing member in the fluid infusion device and the sensed member from the support device when the fluid infusion device is received in the support device.
Figure 6:
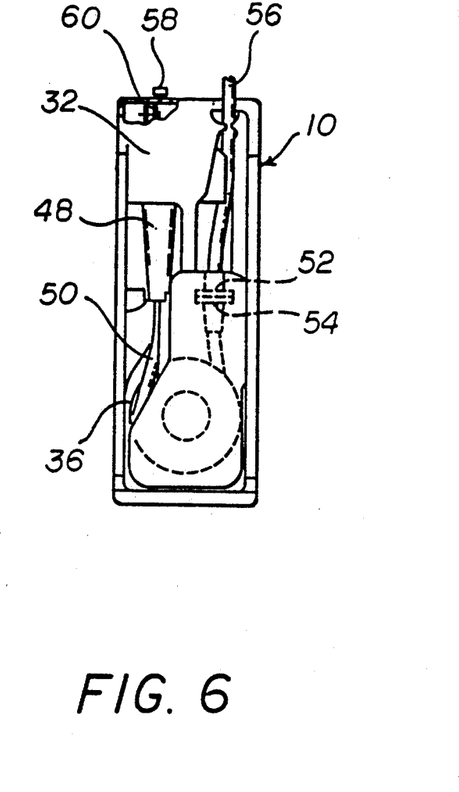
FIG. 6 is a side diagrammatic view, partially in cross section, of the preferred form of the fluid infusion device diagrammatically showing the preferred position of the sensing member relative to the sensed member when the fluid infusion device is received in the support device.

As shown in FIG. 2, the upper channel 26 of the support device 12 preferably includes a sensed member 58 therein. The sensed member 58 is preferably positioned so that it will be located immediately adjacent to the top surface of the housing assembly 31 when the fluid insertion device 10 is received in the device receiving compartment 18 of the support device 12 as shown in FIGS. 5 and 6. A preferred form of the sensed member is a magnetic field source composed of 88% strontium ferrite and 12% #6 nylon having a magnetic strength of about 400 to 500 gauss at the surface edge. This type of magnet is available from Tengam Engineering of Ostsego, Mich., U.S.A.

Figure 7:
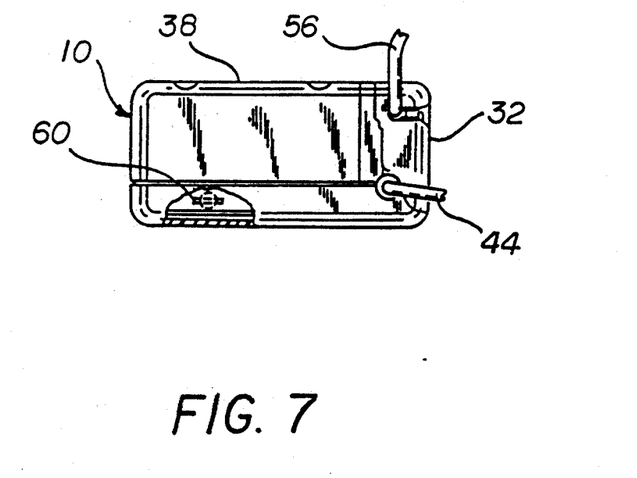
FIG. 7 is a top view, partially in cross section, showing the preferred position of the sensing member in the preferred form of the fluid infusion device.

The housing assembly 31 of the present invention includes a sensing member 60 positioned along the top, inner surface as shown in FIGS. 5-7. The preferred sensing member 60 is a three pin digital magnetoresistive sensor, such as part No. SS21PE, available from Microswitch Inc., of Freeport, Ill., U.S.A. This type of sensing member 60 has been found to be particularly advantageous because it has an omnipolar magnetic feature which allows it to be activated or released by either the north or south pole of the sensed member 58. Testing of the preferred forms of the sensed member 58 and sensing member 60 indicate that the respective members may be misaligned up to about 0.1 inch without affecting the direction of the sensed member 58 by the sensing member 60.

Figure 8:
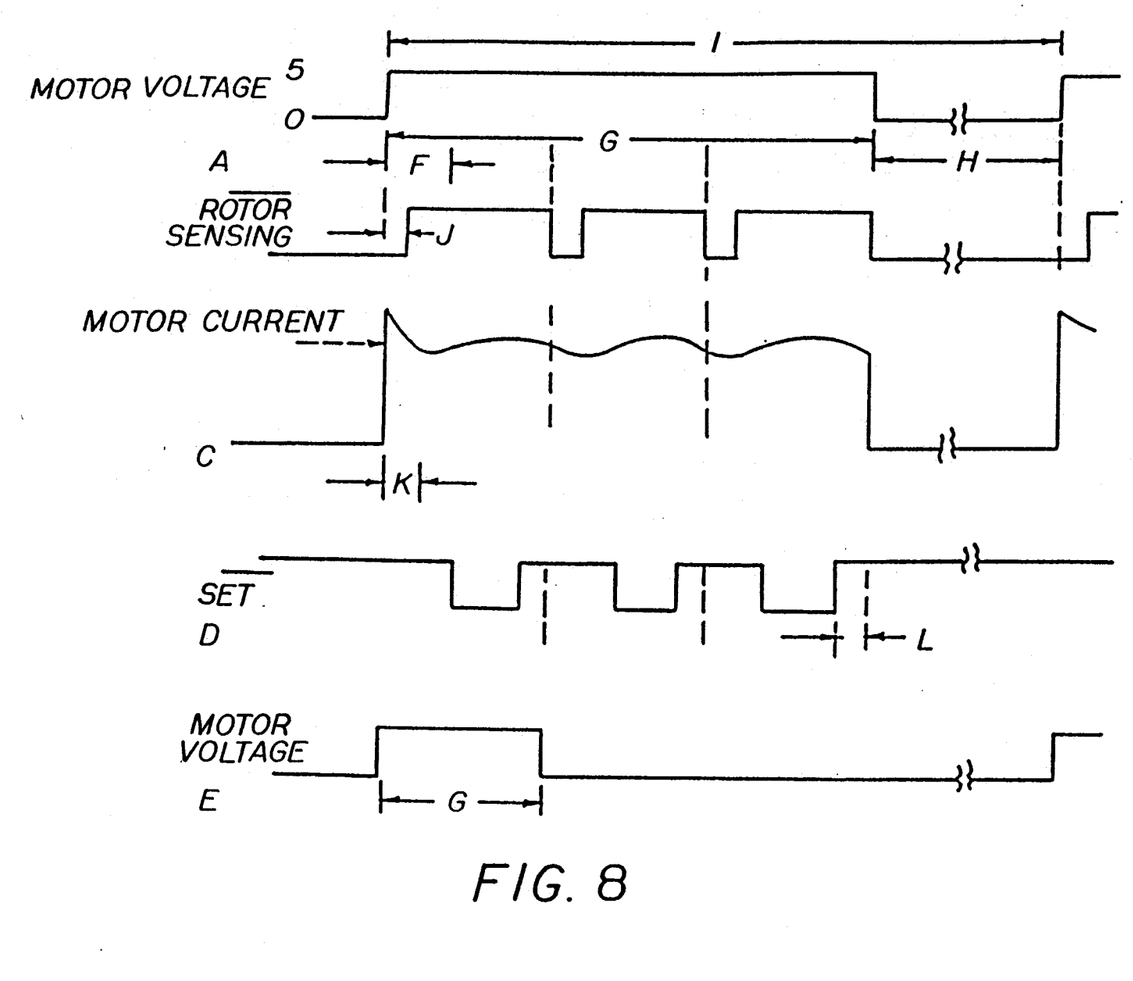
FIG. 8 is a timing diagram illustrating various signals used in the present invention.

As described briefly above, the motor unit 62 of the preferred form of the fluid infusion device 10 provides an intermittent motor operation with the periodicity or cycle time of the intermittent operation being regulated to adjust to the desired rate of fluid delivery as disclosed more fully in U.S. Pat. No. 4,884,013. The operation of the motor unit 62 is preferably cyclical and will be explained with respect to timing diagrams of FIG. 8. Graph A of FIG. 8 illustrates the motor voltage of the enteral fluid delivery system. The motor voltage is turned on and operated for a time period G which is regulated by detecting the rotation of the rotor 36, in the case of Graph A for one complete revolution. During one complete revolution, represented by motor voltage period G, all three rotor magnets pass the magnetic field detector which is located adjacent to the rotor 36 in the housing assembly 31 and are sensed thereby. Curve B in FIG. 8 illustrates the output signal from the rotor magnet sensing magnetic field detector which occurs during the cycle of operation indicted by motor voltage G. During an initial period of approximately 0.45 seconds designated F in FIG. 8, the operation of the rotor sensing magnetic field detector is inhibited by software in microcomputer so that the initial on period J of the magnetic field detector is not responded to by the control program. Thereafter, during one complete revolution of the rotor, the signal from the detector goes to zero as each magnet is encountered by the detector. Upon detection of the third magnet, at the end of period G, the motor voltage is turned off. In accordance with the preferred embodiment of the present invention, the unit repeats the cyclical operation a time period I (the cycle time) after initiation of the first operation. The time period H during which there is provided no motor voltage is permitted to be variable, since it depends on the actual time taken for rotation of the rotor and the selected interval I. The interval I is selected according to the rate of fluid delivery which is set by the operator with the preferred form of the infusion device.

The motor unit 62 operates under the control of a microcomputer which is provided with first and second control programs. The motor unit 62 controls the operation and rotation of the rotor 36. A programmable interval timer is provided for operating and initiating the microcomputer. A clock, preferably operating at approximately 4 Mhz, provides clock pulses to the system. The various controls of the unit are provided as input signals which ground various input terminals of the microcomputer to thereby signal the operators input instructions. The LED display 42 is driven by the microcomputer. Additional inputs to the microcomputer are provided by the three magnetic field sensors which detect the magnetized mounting member 52; the magnets on the rotor 36 and the sensed member 58 on the support device 12. Likewise, a drop detector is connected to provide input signals to the microcomputer. An AC power rectifier is provided for AC operation and battery charging. Portable DC operation is available using a NiCAD battery. The AC circuit is arranged to charge the DC battery when the unit is connected to AC power. A low battery and dead battery detector circuit is provided to signal the microcomputer that the battery needs recharging.

The microcomputer provides an output motor signal which is coupled by transistor to a plurality of switching transistors. The transistor turns on the power supply to the motor voltage regulator when the motor unit 62 is to be operated and the transistor short circuits the motor unit 62 to lock it into position when the motor signal is no longer present. The switching transistor which is provided with a power signal by the transistor, operates to supply current to the motor system and the other electronic systems by the voltage regulator when the power is turned on. The motor unit 62 is provided with a fail safe circuit which creates a short circuit when the motor unit 62 is operated for an excessive period of time as disclosed more fully in U.S. Pat. No. 4,833,379. The short circuit causes a fuse to open thereby disabling the motor unit 62 when continuous motor operation occurs, to avoid providing excess enteral fluid to a patient.

Figure 4:
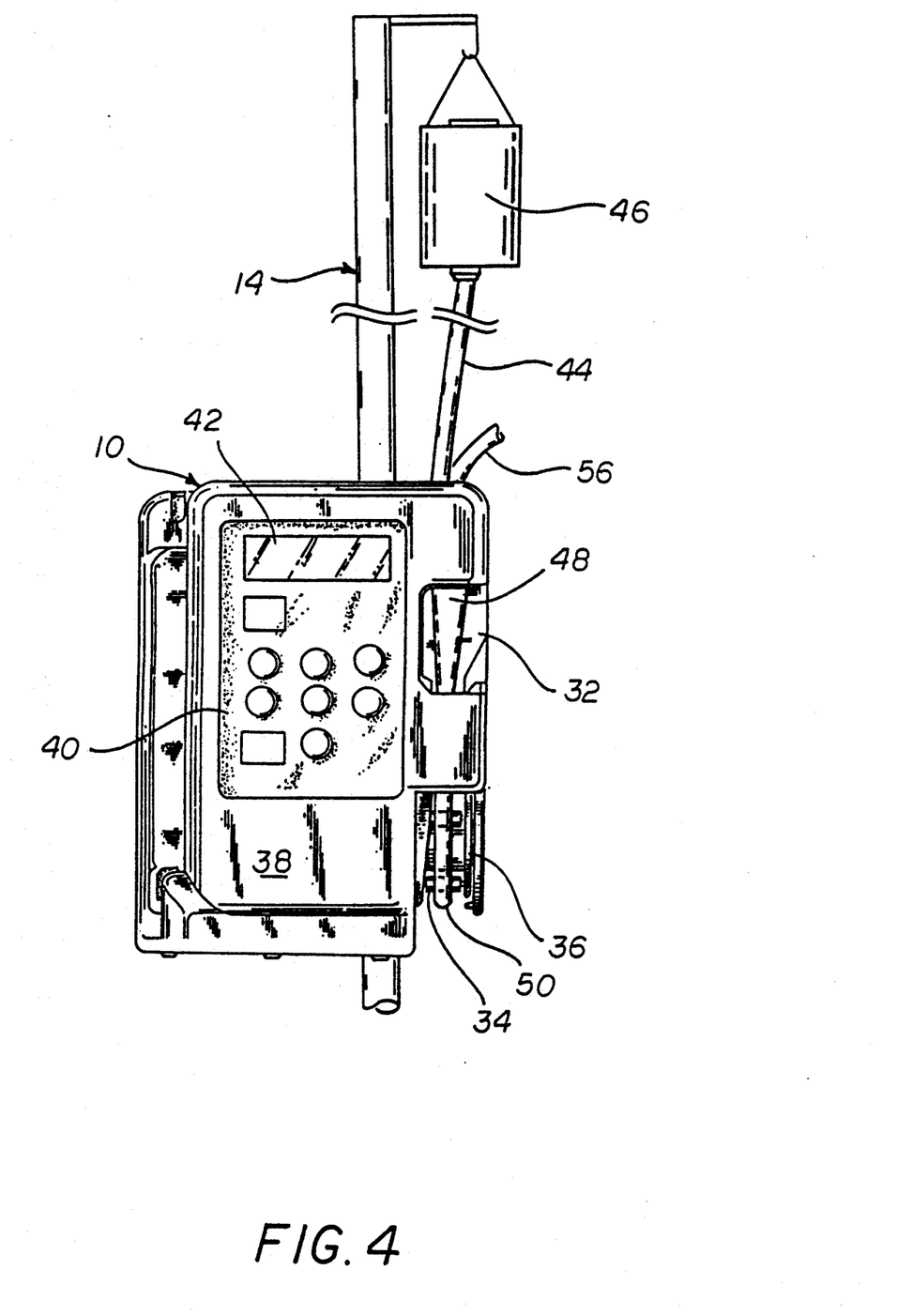
FIG. 4 is a front perspective view of a fluid infusion device in accordance with the present invention mounted on a charger unit and an IV pole.

The foregoing is illustrative of the preferred form of the fluid infusion device 10 and support device 12. When the fluid infusion device 10 is used in a non-ambulatory setting, without the support device 12 (FIG. 4), the sensing member 60 is not activated and there is no additional input provided to the microcomputer. In this situation, the cycle time or period I (FIG. 8) may vary from about 450 seconds for each rotor magnet sensed to provide a fluid rate of 1 ml/hr to about 6.75 seconds for the sensing of three rotor magnets to provide a fluid rate of 200 ml/hr. Other illustrative cycle times are about 9 seconds for the sensing of a single rotor magnet to provide a fluid rate of 50 ml/hr. and about 13.5 seconds for the sensing of three rotor magnets to provide a fluid rate of 100 ml/hr. As stated previously, in this situation, the fluid infusion device 10 is operating in the manner disclosed in U.S. Pat. No. 4,884,013. This is because the first control program in the microcomputer is selected based on the fluid pressure created in the pump tube 50 when the fluid reservoir 46 is extended above the infusion device on the IV pole 14 as shown in FIG. 4.

Figure 3:
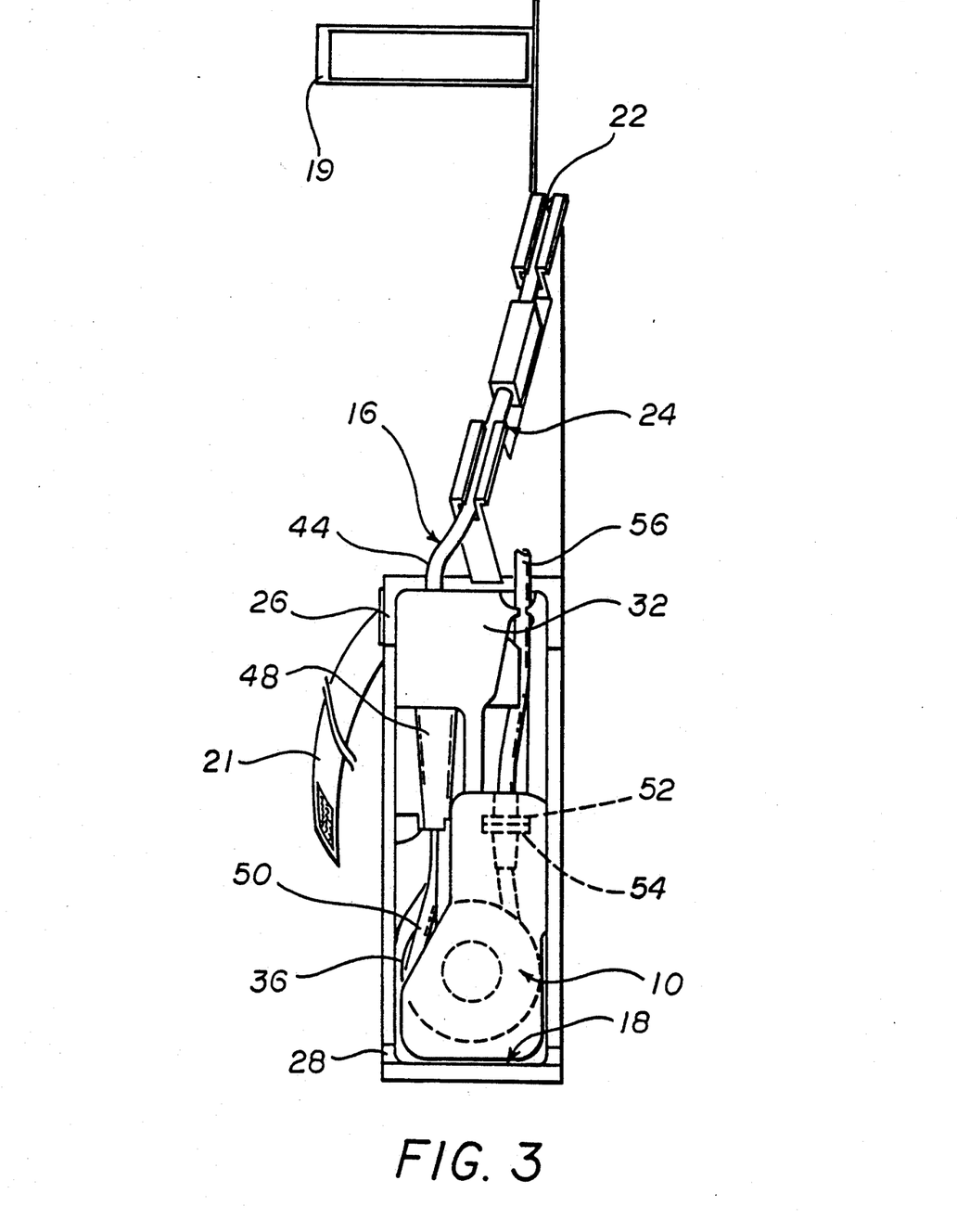
FIG. 3 is a side perspective view of the medical fluid delivery system of FIG. 1.

When the infusion device is used with the support device 12 as shown in FIGS. 1-3, the fluid pressure in the pump tube 50 is significantly lower. Therefore, the pump tube 50 will contain less fluid between the rollers 34 of the rotor 36 and less fluid will be delivered to the patient unless the operation of the motor unit 62 is increased to increase the rotation of the rotor 36 accordingly. As best shown in FIGS. 1 and 2, when the fluid infusion device 10 is used with the support device 12, the bottom of the fluid reservoir 46 is positioned only slightly above the rotor 36 of the fluid infusion device 10 and therefore, the fluid pressure within the pump tube 50 is significantly reduced as compared to when the fluid reservoir 46 is on the IV pole.

The sensing member 60 of the present invention provides an indirect and on/off indication that the fluid infusion device 10 is being used in an ambulatory manner. Therefore, when the fluid infusion device 10 is placed in the support device as shown in FIGS. 1 and 2, the magnet or sensed member 58 on the support device 12 is sensed by the magnetic field detector or sensing member 60 in the fluid infusion device 10. When the sensing member 60 is activated by the sensed member 58, the sensing member 60 provides an input signal to the microcomputer to switch the microcomputer from the first control program to the modified or second control program. In the preferred form of the present invention, the second control program may be either a subprogram of the first control program or a completely separate control program. In either form, the second control program decreases the cycle time (Period I in FIG. 8) to account for the reduced fluid pressure within the pump tube 50. With the present invention, the cycle time is decreased from about 5% to about 10% and more preferably 8.85% so that for a 1 ml/hr. fluid delivery rate, a single rotor magnet is sensed approximately every 410 seconds and for a 200 ml/hr. fluid delivery rate, three rotor magnets are sensed approximately every 6.16 seconds. The other cycle times are similarly reduced such that for a fluid delivery rate of 400 ml/hr., three rotor magnets are sensed approximately every 3.08 seconds when the sensing member 60 is activated as compared to approximately every 3.38 seconds when the sensing member 60 is not activated.

In addition to the above-described preferred form of the present invention, it is anticipated that the sensing member 60 may be used on nearly any medical fluid infusion device 10 and the sensed member 58 may be mounted directly on a portion of the fluid delivery set 16. Additionally, the sensing member 60 may be modified to provide a continuous input signal to the microprocessor wherein the signal indicates the distance between the fluid reservoir 46 and the fluid infusion device 10 or rotor 36. This may be accomplished with various sensors such as an infrared sensor, a fluid pressure sensor or it may be part of the input information required from the user prior to operation of the fluid infusion device 10. The control program may then be modified to adjust the cycle time of the rotor 36 to provide an accurate infusion rate based on the known fluid pressures created in the pump tube 50 at various distances above the fluid infusion device 10 or rotor 36.

It will be apparent from the foregoing, while particular embodiments of the invention have been illustrated and described, various modifications may be made thereto without departing from the spirit and scope of the present invention. Accordingly, it is not intended that the invention be limited, except as defined by the appended claims.

What is claimed is:

1. A medical fluid delivery system for the delivery of a medical fluid to a patient at a controlled rate; said system comprising:
   a fluid delivery set including a reservoir means for containing fluid, a support structure for supporting said reservoir means, and a tube means forming a fluid flow pathway therethrough which is in fluid flow connection with said reservoir means;
   a pump means for moving fluid through said fluid flow pathway and including a control means for adjustably controlling operation of said pump means; and
   sensor means for determining the position of said pump means relative to said fluid delivery set, said sensor means including a sensing member and a sensed member, one of said sensing member and said sensed member being formed as part of said pump means and the other being formed as part of said support structure;
   whereby, said control means adjusts operation of said pump means in accordance with the position of said pump means relative to said fluid delivery set as determined by said sensor means to ensure movement of fluid through said fluid flow pathway at said controlled rate.

2. A medical fluid delivery system according to claim 1 wherein said sensed member is a magnet and said sensing member is a magnetic field detector.

3. A medical fluid delivery system according to claim 2 wherein said control means causes operation of said pump means in a first mode of operation when said magnet is detected by said magnetic field detector, and in a second mode of operation when said magnet is not detected by said magnetic field detector.

4. A medical fluid delivery system according to claim 3 wherein said pump means includes a rotary member having a plurality of rollers thereon and a portion of said tube means of said fluid delivery set is positioned adjacent said rollers of said rotary member,
   whereby, rotation of said rotary member of said pump means causes movement of fluid through said fluid flow pathway formed by said tube means.

5. A medical fluid delivery system according to claim 4 wherein said rotary member rotates at a first speed when said pump means is in said first mode of operation and at a second speed when said pump means is in said second mode of operation.

6. A medical fluid delivery system according to claim 5 wherein said first speed is greater than said second speed.

7. A medical fluid delivery system according to claim 2 wherein said support structure includes means for attaching said pump means thereto.

8. A medical fluid delivery system according to claim 7 wherein attachment of said pump mans to said support structure positions said magnet relative to said magnetic field detector such that said magnet can be detected by said magnetic field detector.

* * * * *